US00PP29371P3

(12) United States Plant Patent
Brown

(10) Patent No.: US PP29,371 P3
(45) Date of Patent: Jun. 12, 2018

(54) ***ABELIA* PLANT NAMED 'LG01'**

(50) Latin Name: ***Abelia*×*grandiflora* hybrid**
Varietal Denomination: LG01

(71) Applicant: Graham Brown, Cobbitty (AU)

(72) Inventor: Graham Brown, Cobbitty (AU)

( * ) Notice: Subject to any disclaimer, the term of this patent is extended or adjusted under 35 U.S.C. 154(b) by 0 days. days.

(21) Appl. No.: 15/530,709

(22) Filed: Feb. 17, 2017

(65) Prior Publication Data

US 2017/0245408 P1 Aug. 24, 2017

(30) Foreign Application Priority Data

Feb. 20, 2016 (AU) ..... 2016/052

(51) Int. Cl.
*A01H 5/00* (2018.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — Samuel R. McCoy, Jr.

(57) ABSTRACT

A new and distinct *Abelia* cultivar named 'LG01' which is characterized by the combination of a compact, freely-branching growth habit with a generally mounded to semi-upright shape, dense foliage, bright yellow juvenile foliage, yellow-green mature foliage, and the stability of these characteristics from generation to generation.

2 Drawing Sheets

Latin name of the genus and species: The Latin name of the genus and species of the novel variety disclosed herein is *Abelia*×*grandiflora* hybrid.

Variety denomination: The inventive cultivar of *Abelia* disclosed herein has been given the variety denomination 'LG01'.

CROSS REFERENCE TO RELATED APPLICATIONS

This application claims priority to the Australian Plant Breeders Rights application number 2016/052, filed on Feb. 20, 2016, which is herein incorporated by reference.

BACKGROUND OF THE INVENTION

Parentage: 'LG01' originated as a chemically-induced partial plant mutation of *Abelia* 'Kaleidoscope' (U.S. Pat. No. 16,988) performed at a plant breeding facility in Cobbitty, New South Wales, Australia. In March of 2014, 500 plants of *Abelia* 'Kaleidoscope' (U.S. Pat. No. 16,988) were treated with Ethyl Methyl Sulphanate, rinsed well, and subsequently evaluated for the occurrence of mutations. Over 20 mutant shoots were identified and propagated. The candidate 'LG01' was initially selected for further evaluation in May of 2014 due to its non-variegated bright yellow leaves. Propagation, pot trials and further field trials continued till final selection in 2015.

Asexual Reproduction: Asexual reproduction of 'LG01', by way of softwood stem cuttings, was first performed in May of 2014 in Cobbitty, New South Wales, Australia. Through ten subsequent generations, the unique features of this cultivar have proven to be stable and true to type.

SUMMARY OF THE INVENTION

The cultivar 'LG01' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'LG01'. These characteristics in combination distinguish 'LG01' as a new and distinct *Abelia* hybrid cultivar:

1. *Abelia* 'LG01' exhibits a freely branching, mounded to semi-upright growth habit with dense foliage; and
2. *Abelia* 'LG01' exhibits bright yellow, glossy juvenile foliage; and
3. *Abelia* 'LG01' exhibits yellow-green, glossy mature foliage; and
4. *Abelia* 'LG01' exhibits reddish stems.

BOTANICAL DESCRIPTION OF THE PLANT

Figure 1:
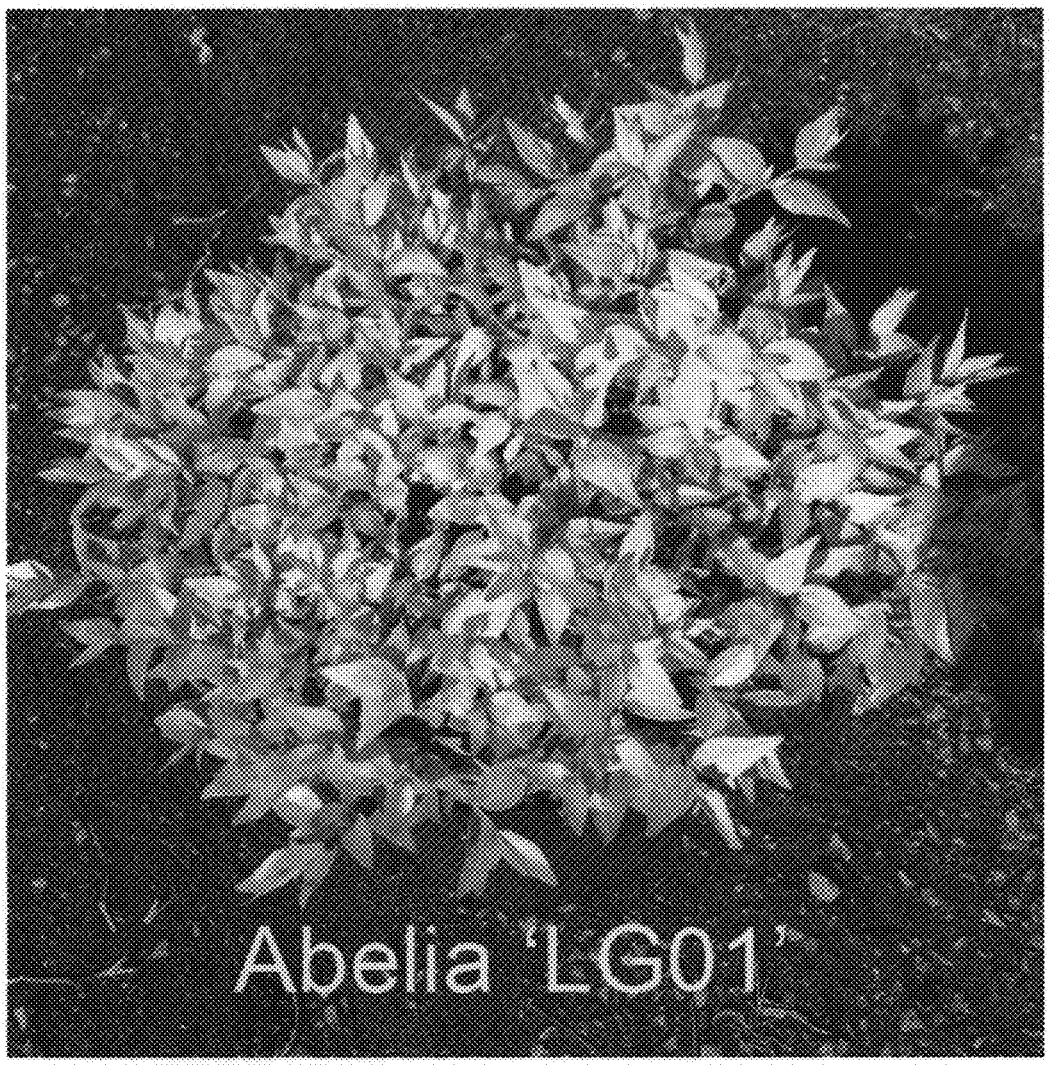
FIG. 1 illustrates, as nearly true as it is reasonably possible to make the same in color photographs of this type, an exemplary 14 month old 'LG01', field-grown in Bellingen, New South Wales, Australia.
Figure 2:
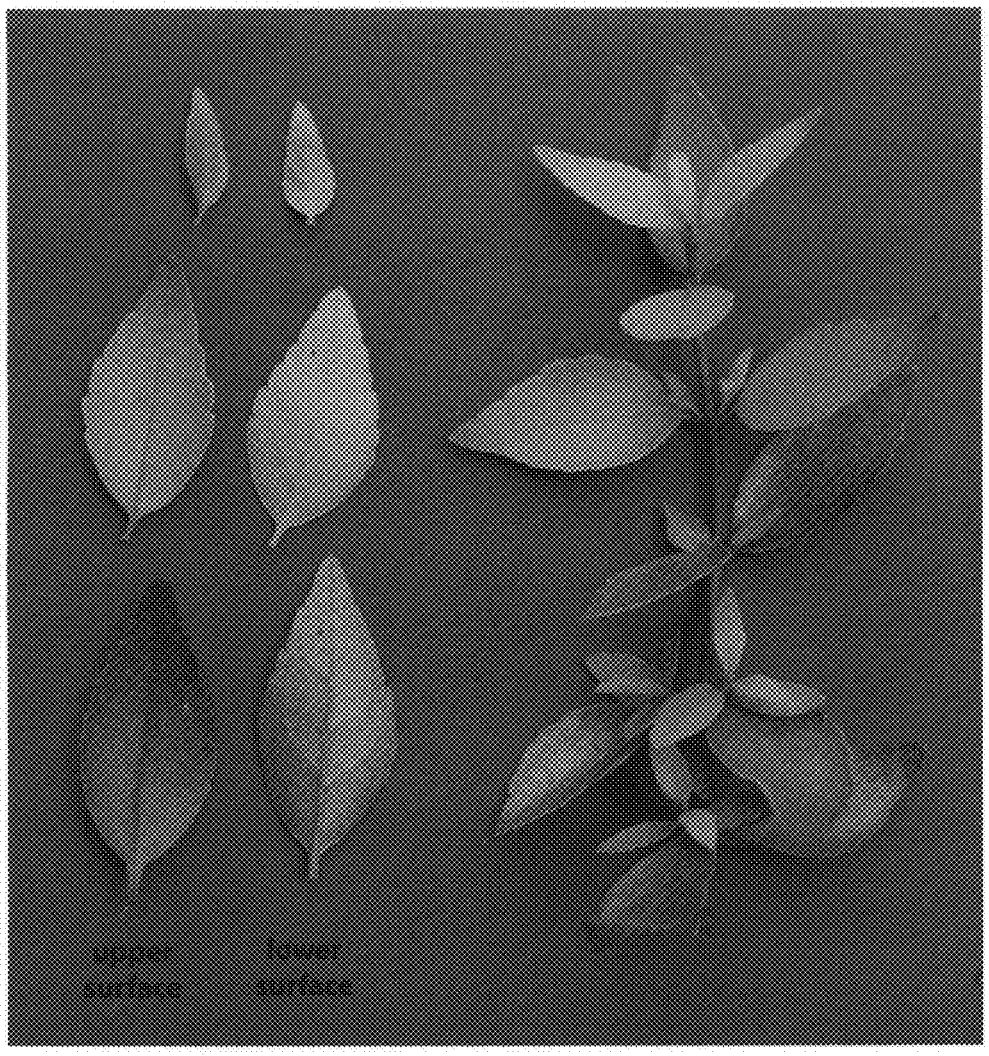
FIG. 2 illustrates, as nearly true as it is reasonably possible to make the same in color photographs of this type, the typical juvenile foliage, mature foliage and lateral branch of 'LG01'.

The following observations and measurements made in February of 2017 and, unless otherwise indicated, describe a 14 month old potted 'LG01' field-grown plant produced in an 8 inch container in Bellingen, New South Wales, Australia. Plants were produced under shade, using conventional production protocols for *Abelia* which consisted of regular overhead irrigation and controlled-release fertilizer applications. No chemical pest or disease measures were utilized in production.

Those skilled in the art will appreciate that certain characteristics will vary with older or, conversely, with younger plants. 'LG01' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2001 edition.

A botanical description of 'LG01' and a comparison with the parent plant and the most similar commercial *Abelia* cultivar known to the inventor, is provided below.

Plant description:

*Growth habit.*—Evergreen to semi-deciduous shrub.

*Plant shape.*—Compact; mounded to semi-upright.

*Average height.*—25 cm as observed; approximately 100 cm when fully matured.

*Average width.*—25 cm as observed; approximately 100 cm when fully matured.

*Plant vigor.*—Moderately vigorous.

*Propagation details.*—Asexual propagation may be accomplished by both softwood and hardwood stem cuttings.

*Time to initiate roots.*—Approximately 21 days are required to initiate roots from a softwood cutting.

*Time to produce a marketable rooted cutting.*—Approximately 10 to 12 weeks when propagated in the spring.

*Disease and pest resistance or susceptibility.*—Neither tolerance nor resistance to normal diseases and pests of *Abelia* have been observed.

*Environmental tolerances.*—Hardy to approximately minus 6 degrees Celsius and tolerant of temperatures to 40 degrees Celsius. Generally drought tolerant once established.

Root system:

*General.*—Fibrous; freely branched and moderately dense rooting.

*Distribution in the soil profile.*—Shallow to moderately deep.

*Texture.*—Smooth.

*Color, juvenile roots.*—Orange-white, nearest to RHS 159C.

*Color, mature roots.*—Greyed-brown, nearest to RHS 165A.

Stems:

*Branching habit.*—One main stem, itself freely branching, and giving rise to numerous lateral branches.

*Main stem.*—Attitude — Erect. Diameter — 8 mm. Color — Greyed-orange, RHS 177B. Texture — Fissured.

*Lateral branches.*—Aspect — Semi-erect and arching towards the distal end. Shape — Rounded. Strength — Weak to moderately strong. Diameter of lateral branches — Averaging 1.7 mm at the base. Internode length on lateral branches — Approximately 13 mm. Texture — Smooth. Color — Greyed-red, RHS 177B. Color at internodes — Orange-red, RHS N34C.

Foliage:

*Arrangement.*—Opposite.

*Attachment.*—Petiolate.

*Division.*—Simple.

*Foliage density on lateral branch.*—Very dense.

*Lamina.*—Dimensions — 27 mm long and 13 mm wide, on average. Thickness — Approximately 1 mm at the midrib. Shape — Ovate. Aspect — Involute. Apex — Acuminate. Base — Rounded. Margin — Crenate. Pubescence, adaxial surface — Glabrous. Texture and luster of adaxial surface — Smooth and glossy. Pubescence, abaxial surface — Glabrous. Texture and luster of abaxial surface — Smooth and moderately glossy. Color — Juvenile foliage, adaxial surface — Yellow-green, RHS 151C; newly emerged foliage is lightly suffused with orange-red, RHS 31A. Juvenile foliage, abaxial surface — Yellow-green, RHS 151C. Mature foliage, adaxial surface — Green, RHS 138A. Mature foliage, abaxial surface — Green, RHS 139C. Venation — Pattern — Pinnate. Color, adaxial surface — Green, RHS 138A. Color, abaxial surface — Green, RHS 139C.

*Petiole.*—Length — 3.2 mm. Width — 1.0 mm. Texture — Glabrous; smooth. Luster — Moderately glossy. Strength — Strong. Color, adaxial surface — Green, RHS 138A. Color, abaxial surface — Green, RHS 138A.

Inflorescence: No flowering has been observed to date.

Flower buds: No flowering has been observed to date.

Flower: No flowering has been observed to date.

Reproductive organs: Not observed.

Seed and fruit: Not observed.

COMPARISON WITH THE PARENT

Plants of the new cultivar 'LG01' may be distinguished from its parent, *Abelia* 'Kaleidoscope' (U.S. Pat. No. 16,988), by the characteristics described in Table 1.

TABLE 1

| Characteristic | 'LG01' | 'Kaleidoscope' |
|---|---|---|
| Presence of leaf variegation. | Absent. | Present. |
| General coloration of the juvenile foliage in spring and summer. | Golden yellow; newly emerged foliage is lightly suffused with orange-red. | Green at and near the midrib and broadly margined with light yellow-green; newly emerged foliage is lightly suffused with orange-red. |
| General coloration of the juvenile foliage in fall and early winter. | Golden yellow; newly emerged foliage is lightly suffused with orange-red. | Green at and near the midrib and broadly margined with a combination of dark greyed-orange and orange-red. |
| General coloration of the mature foliage. | Light green. | Intermediate foliage is dark green at and near the midrib and broadly margined with light yellow-green; occasionally suffused with greyed-orange to orange-red. |

COMPARISON WITH THE CLOSEST KNOWN COMMERCIAL COMPARATOR

Plants of the new cultivar 'LG01' may be distinguished from the most similar known commercial comparator, *Abelia* 'Saxon Gold' (U.S. Pat. No. 15,178), by the characteristics described in Table 2.

TABLE 2

| Characteristic | 'LG01' | 'Saxon Gold' |
|---|---|---|
| General coloration of the juvenile foliage in spring and summer. | Bright yellow; newly emerged foliage is lightly suffused with orange-red. | A combination of chartreuse and copper; lightly suffused with orange-red. |

TABLE 2-continued

| Characteristic | 'LG01' | 'Saxon Gold' |
|---|---|---|
| General coloration of the mature foliage. | Yellow-green. | A combination of chartreuse and copper. |

That which is claimed is:

1. A new and distinct cultivar of *Abelia* plant named 'LG01', substantially as described and illustrated herein.

* * * * *